(12) United States Patent
Zoffoli et al.

(10) Patent No.: US 11,872,449 B2
(45) Date of Patent: Jan. 16, 2024

(54) METHOD FOR CONTROLLING VARIATION OF WORKOUT PARAMETERS OF A USER ON AN EXERCISE MACHINE FOR STRENGTH WORKOUT AND RELATED SYSTEM

(71) Applicant: TECHNOGYM S.p.A., Cesena (IT)

(72) Inventors: Luca Zoffoli, Cesena (IT); Roberto Nicoletta, Cesena (IT)

(73) Assignee: TECHNOGYM S.p.A., Cesena (IT)

( * ) Notice: Subject to any disclaimer, the term of this patent is extended or adjusted under 35 U.S.C. 154(b) by 275 days.

(21) Appl. No.: 17/516,846

(22) Filed: Nov. 2, 2021

(65) Prior Publication Data

US 2022/0143466 A1 May 12, 2022

(30) Foreign Application Priority Data

Nov. 6, 2020 (IT) .................. 102020000026512

(51) Int. Cl.
*A63B 24/00* (2006.01)
*A63B 21/005* (2006.01)

(52) U.S. Cl.
CPC ...... *A63B 24/0087* (2013.01); *A63B 21/0058* (2013.01); *A63B 24/0075* (2013.01);
(Continued)

(58) Field of Classification Search
CPC ............ A63B 24/0087; A63B 21/0058; A63B 24/0075; A63B 2024/0068; A63B 2024/0093; A63B 2225/20; G16H 20/30
See application file for complete search history.

(56) References Cited

U.S. PATENT DOCUMENTS 10,688,345 B1 * 6/2020 Lynch ................. G16H 20/30
2007/0232455 A1 * 10/2007 Hanoun ............ A63B 24/0084
482/8

(Continued)

FOREIGN PATENT DOCUMENTS

| CA | WO2006042420 A1 * | 11/2005 | ............... A61B 5/22 |
| WO | 2006/042420 A1 | 4/2006 | |
| WO | 2008/030484 A2 | 3/2008 | |

OTHER PUBLICATIONS

Search Report for IT2020000026512 dated Jul. 15, 2021, Munich, DE.

*Primary Examiner* — Andrew S Lo
*Assistant Examiner* — Andrew M Kobylarz
(74) *Attorney, Agent, or Firm* — ArentFox Schiff LLP; Michael Fainberg

(57) ABSTRACT

A method for controlling variation of workout parameters of a user on an exercise machine includes checking, by a data processing module of a remote electronic calculator operatively connected to the exercise machine that a trigger condition of a cycle of workout progression steps is met. If the trigger condition is met, the method includes acquiring the last workout progression step performed by the user, identifying a successive workout progression step, setting workout parameters associated with the workout progression step to be performed, the workout progression step having associated a variation of at least one workout parameter of the user for updating a previously set value of the at least one workout parameter, updating the previously set value according to the variation of the at least one workout parameter, and sending the workout parameters to a data processing unit of the exercise machine value.

21 Claims, 6 Drawing Sheets

(52) U.S. Cl.
CPC .............. *A63B 2024/0068* (2013.01); *A63B 2024/0093* (2013.01); *A63B 2225/20* (2013.01)

(56) References Cited

U.S. PATENT DOCUMENTS

| | | | | |
|---|---|---|---|---|
| 2014/0214446 | A1* | 7/2014 | Nusbaum | A63B 24/0062 |
| | | | | 705/2 |
| 2017/0319941 | A1* | 11/2017 | Smith | A63B 21/06 |
| 2018/0353812 | A1* | 12/2018 | Lannon | G16H 20/30 |
| 2020/0001134 | A1* | 1/2020 | Rauhala | A61B 5/4815 |
| 2020/0160961 | A1* | 5/2020 | Wadhawan | A63B 24/0059 |
| 2020/0179757 | A1* | 6/2020 | Toivonen | G16H 10/20 |
| 2020/0261011 | A1* | 8/2020 | Seppänen | G16H 20/30 |
| 2021/0085219 | A1* | 3/2021 | Liv | A61B 5/0022 |

\* cited by examiner

METHOD FOR CONTROLLING VARIATION OF WORKOUT PARAMETERS OF A USER ON AN EXERCISE MACHINE FOR STRENGTH WORKOUT AND RELATED SYSTEM

CROSS-REFERENCE TO RELATED APPLICATION

This application claims priority to Italian Patent Application No. 102020000026512 filed on Nov. 6, 2020, the entire contents of which is hereby incorporated in its entirety by reference.

FIELD OF THE INVENTION

The present invention relates to the field of a person's health and fitness, and in particular to a method for controlling at least one variation of workout parameters of a user during the workout on an exercise machine for strength workout, and to a related system.

BACKGROUND OF THE INVENTION

In sports and fitness, a strength workout requires respecting the principle of progressivity.

Such a principle affirms that a workout is effective only if the features thereof are adequate for the level of physical condition of the user.

For this reason, the parameters defining a workout method are to vary over time to accommodate the adaptations of the user (for example, improvement of performance).

Moreover, respecting the principle of progressivity must also take into consideration the goals for which the workout is performed.

Such goals are different from user to user and may for example, be toning, increasing strength, maintaining a youthful appearance, losing weight.

In order to improve at the performance level, today the need is strongly felt to have available a method for controlling at least one variation of workout parameters of a user on an exercise machine for strength workout which allows performing strength workout exercises in a controlled manner, thus ensuring as performing and reliable an execution as possible by the user in compliance with the principle of workout progressivity.

SUMMARY OF THE INVENTION

It is the object of the present invention to devise and provide a method for controlling at least one variation of workout parameters of a user on an exercise machine for strength workout which allows obviating the drawbacks indicated above with reference to the prior art, in particular which allows controlling the physical exercise, ensuring the most performing and reliable execution by the user in compliance with the principle of workout progressivity.

Preferred embodiments are also described.

The present invention also relates to a system implementing such a method.

BRIEF DESCRIPTION OF THE DRAWINGS

Further features and advantages of the method and such a system according to the invention will become apparent from the following description of preferred embodiments, given by way of indicative, non-limiting example, with reference to the accompanying drawings, in which.

It is worth noting that equivalent or similar elements are indicated by the same numerical and/or alphanumerical reference in the aforesaid drawings.

DETAILED DESCRIPTION

With reference to the aforesaid drawings, a system 200 for controlling at least one variation of workout parameters of a user on an exercise machine for strength workout, later also control system 200 or simply system 200, according to the present invention, is now described.

Figure 1:
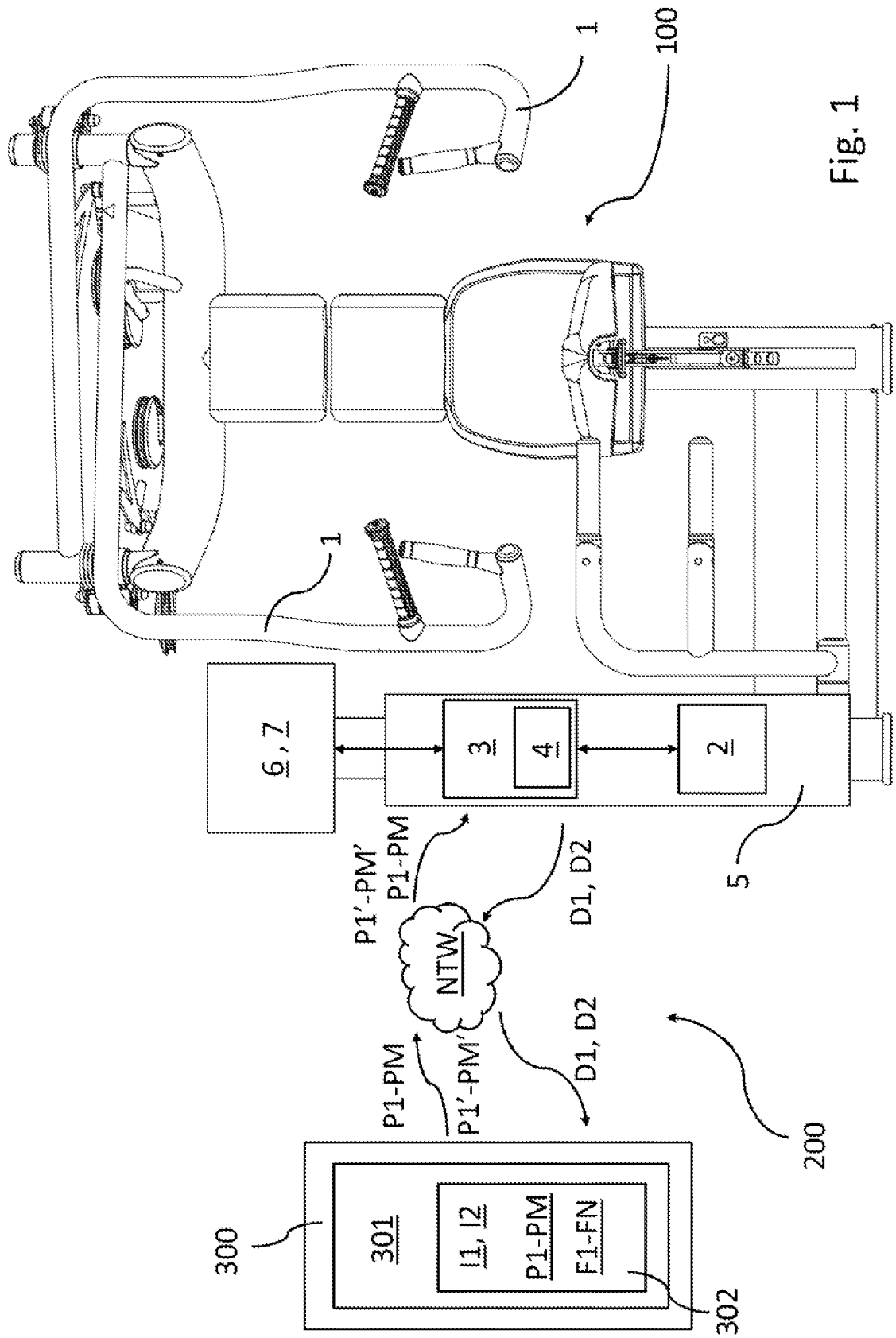
FIG. 1 diagrammatically shows a system for controlling at least one variation of workout parameters of a user on an exercise machine for strength workout, according to the present invention.

With reference to FIG. 1, the system 200 comprises at least one exercise machine 100 for strength workout which can be used by a user to perform physical activity.

An exercise machine 100 for strength workout is any exercise machine in which the user handles an exercise or work load when performing an exercise, thus muscularly building one or more parts of the body such as, for example, the chest, shoulders, upper limbs, lower limbs, and so on.

Figure 2:
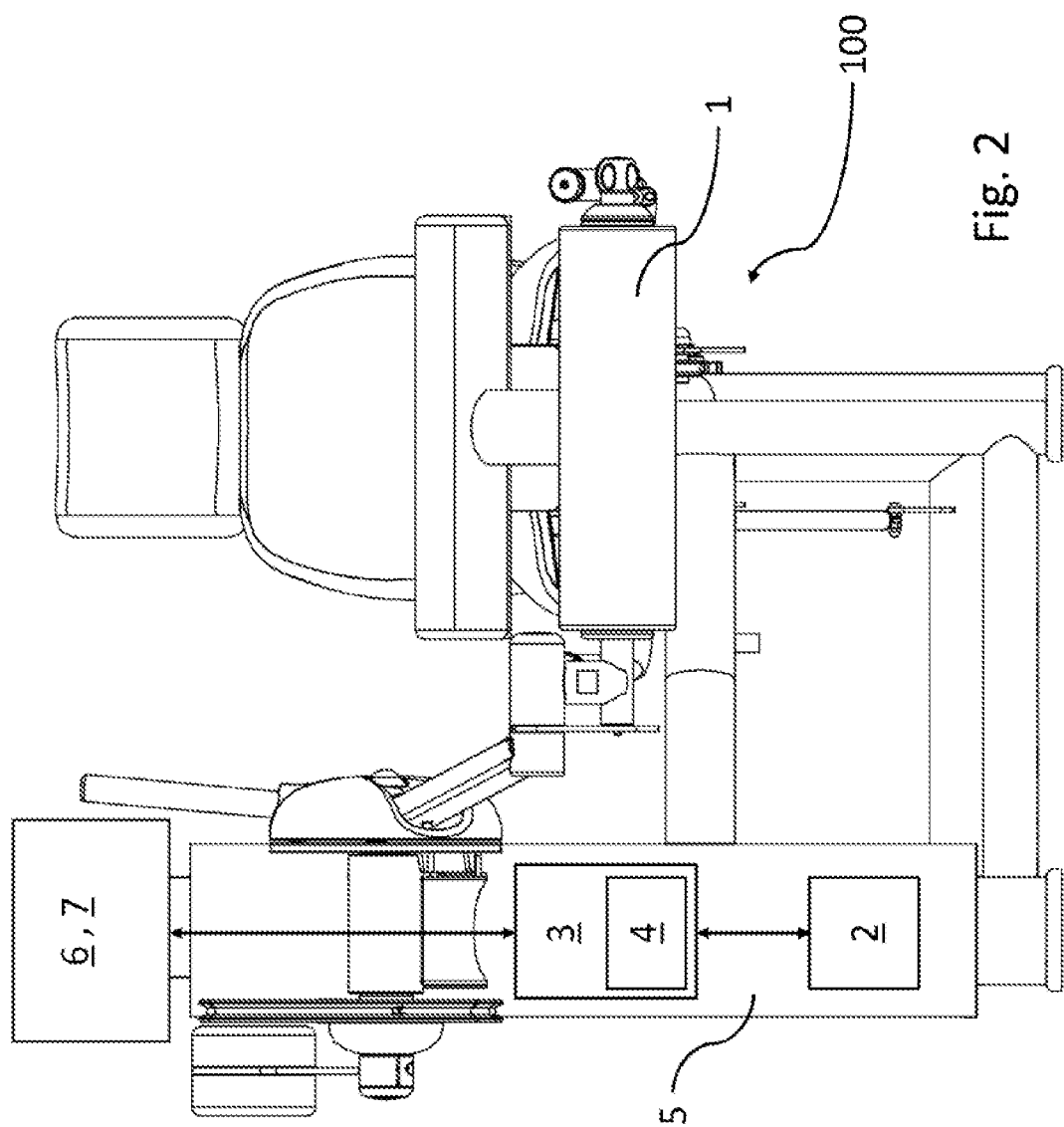
FIG. 2 shows an exercise machine for strength workout which can be employed in the system in FIG. 1.
Figure 3:
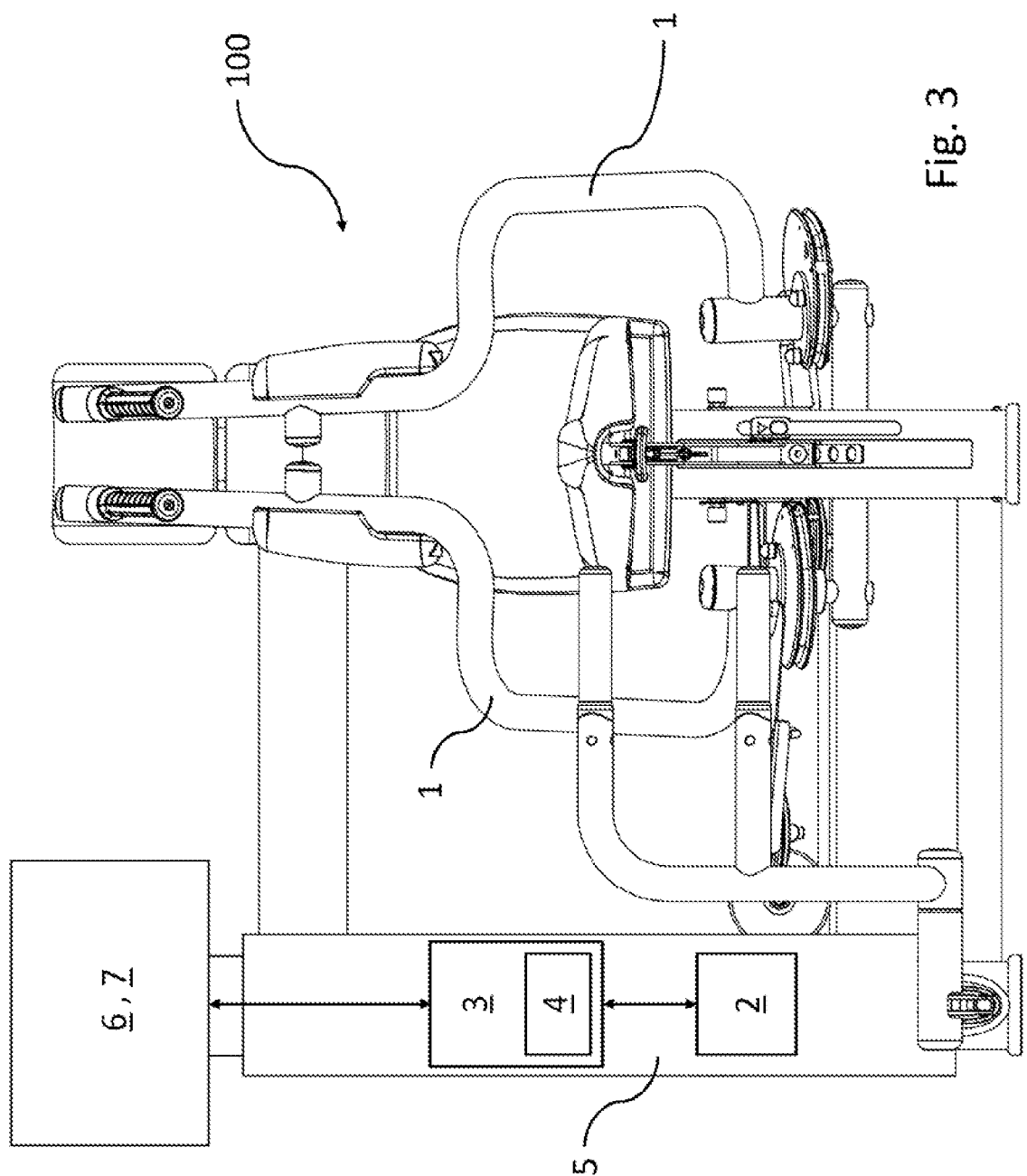
FIG. 3 shows another exercise machine for strength workout which can be employed in the system in FIG. 1.

The example in the drawings shows exercise machines for strength workout of the upper limbs, a chest press in FIG. 1 and a pectoral machine in FIG. 3, and an exercise machine for strength workout of the lower limbs, a leg extension in FIG. 2, respectively.

With reference to any FIGS. 1 to 3, the exercise machine 100 for strength workout comprises at least one movable element 1 operable by a user to execute a strength exercise by handling a respective exercise load.

The exercise machine 100 for strength workout further comprises at least one motor 2 (diagrammatically shown in the drawings) operatively connected, for example by means of mechanical kinematic mechanisms, to the at least one movable element 1.

The at least one motor 2 is configured to exert, on the at least one movable element 1, a resistive force representative of an exercise load which the user may handle during the execution of the exercise by actuating the at least one movable element 1.

The at least one motor 2 is any motor in which the control allows applying such a resistive force, such as, for example, an electric motor, an electromagnetic motor, and so on.

Returning to the at least one movable element 1, according to any of the embodiments in FIGS. 1 to 3, it is worth noting that the at least one movable element 1 is operable by the user in a first movement direction (so-called concentric movement) which simulates the lifting of a gravitational load (exercise or work load) and in a second movement direction (so-called eccentric movement), in a direction opposite to the first movement direction, which simulates the return of the gravitational load (exercise load) to a starting position.

It is worth noting that the user is capable of a range of motion (ROM) during the actuation of the at least one first movable element 1.

In the first movement direction, such a range of motion (concentric movement) ranges between a first starting position, in which the machine is configured to start raising the exercise load, and a second movement end position, in which the user has moved the movable element against the resistance provided by the exercise load.

In a completely complementary manner, the range of motion in the second movement direction (eccentric movement) is comprised between the second position (end of movement of the preceding step) and the first starting position, in which the machine is configured to start raising the exercise load.

In the example in FIGS. 1 and 3, the at least one movable element 1 is a first lever, which is operable by a first upper limb of the user.

In this example, the exercise machine 100 further comprises at least one second lever, indicated again by numerical reference 1, which is operable by a second upper limb of the user.

In the example in FIG. 2, the at least one movable element 1 is a further lever, which is operable by both lower limbs of the user.

The exercise machine 100 for strength workout further comprises a data processing unit 3, for example a microcontroller or a microprocessor.

The data processing unit 3 is operatively connected to said at least one electric motor 2.

The exercise machine 100 for strength workout further comprises a memory unit 4 operatively connected to the data processing unit 3.

The memory unit 4 may be inside (as diagrammatically shown in FIGS. 1 to 3) or outside the data processing unit 3 (embodiment not shown in the drawings).

By loading and executing one or more program codes stored in the memory unit 4, the data processing unit 3 is configured to control the exercise machine 100.

In particular, the data processing unit 3 is configured to control the at least one motor 2.

Moreover, as described later, the data processing unit 3 is configured to communicate with a remote electronic calculator 300 (shown diagrammatically in FIG. 1).

In greater detail, the data processing unit 3 is configured to receive setting parameters of the exercise machine 100 required to perform an exercise, from the remote electronic calculator 300.

Such setting parameters may be, for example the number of repetitions to be performed, the number of series to be performed, the recovery time between each series, the exercise load for each series.

Moreover, the data processing unit 3 is configured to receive, from the remote electronic calculator 300, workout parameters of a user on the exercise machine 100 provided within the scope of the execution, by the remote electronic calculator 300, of steps of a method for controlling at least one variation of workout parameters of a user on an exercise machine for strength workout, according to the present invention.

Such workout parameters of a user on the exercise machine 100 are described later.

Moreover, the data processing unit 3 is configured to automatically send, to the remote electronic calculator 300, at the end of each exercise performed by the user on the exercise machine 100, first time data D1 of the exercise performed by the user on the exercise machine 100 and second data D2 representative of a strength workout status achieved by the user with the exercise performed.

The first time data D1 of the exercise performed by the user and the second data D2 representative of a strength workout status achieved by the user with the exercise performed are described in greater detail below.

Returning to any FIGS. 1 to 3, in an embodiment, the exercise machine 100 further comprises a housing 5 inside of which the at least one electric motor 2, the data processing unit 3 and the memory unit 4 are accommodated.

Again, with reference to FIGS. 1 to 3, in an embodiment, in combination with any of those described above, the exercise machine 100 further comprises a user interface 6 operatively connected to the data processing unit 3.

In this regard, it is worth noting that the data processing unit 3 is further configured to control the exercise machine 100 for strength workout on the basis of commands imparted by the user by means of the user interface 6.

In an embodiment, the user interface 6 may be of the touchscreen type.

In a further embodiment, alternative to the preceding one, the user interface 6 may be a push-button keyboard.

In an embodiment shown in the drawings, the user interface 6 is installed on housing 5.

In an embodiment, in combination with any of those described above, shown in any FIGS. 1 to 3, the exercise machine 100 for strength workout further comprises a display module (display) 7 operatively connected to the data processing unit 3.

The display module 7 may be used by the user during interaction with the user interface 6.

Indeed, the display module 7 is configured to show content to the user representative of the use of the exercise machine 100 for strength workout, for example authentication screen, initial menu screen for setting the workout, screen with parameters and/or charts updated during the execution of the workout, workout summary screen, and so on.

In an embodiment shown in FIGS. 1 to 3 in which the user interface 6 is of the touchscreen type, the display module 7 may coincide with the user interface 6.

It is worth noting in this embodiment that the display module 7 is configured to also show the user interface 6 to the user, in addition to the contents representative of the use of the exercise machine 100 for strength workout (of which some examples were provided above).

According to a further embodiment, alternative to the preceding one and not shown in the drawings, the display module 7 instead is separate from the user interface 6.

Returning to FIG. 1, the system 200 further comprises a remote electronic calculator 300, for example a cloud server, operatively connected to the at least one exercise machine 100 for strength workout.

The remote electronic calculator 300 is operatively connected to the at least one exercise machine 100 for strength workout in wired mode or in wireless mode by means of a data communication network NTW, for example Internet.

The remote electronic calculator 300 comprises a data processing module 301, for example a microcontroller or microprocessor.

The data processing module 301 of the remote electronic calculator 300 is operatively connected to the data processing unit 3 of the exercise machine 100.

The remote electronic calculator 300 further comprises a memory module 302 operatively connected to the data processing module 301.

The memory module 302 may be inside (as diagrammatically shown in FIGS. 1 to 3) or outside the data processing module 301 (embodiment not shown in the drawings).

By loading and executing one or more program codes stored in the memory module 302, the data processing module 301 is firstly configured to control the remote electronic calculator 300.

Moreover, the data processing module 301 is configured to send, to the data processing unit 3 of the exercise machine 100, setting parameters of the exercise machine 100 stored in the memory module 302, which are required to perform an exercise.

Again, the data processing module 301 is configured to perform steps of a method for controlling at least one variation of workout parameters of a user on an exercise machine 100 for strength workout, as described later, which are left to the remote electronic calculator 300.

In this regard, in greater detail, within the scope of the execution of operating steps of the aforesaid control method, the data processing module 301 of the remote electronic calculator 300 is configured to control at least one variation of workout parameters of a user on the exercise machine 100 for strength workout.

Figure 4:
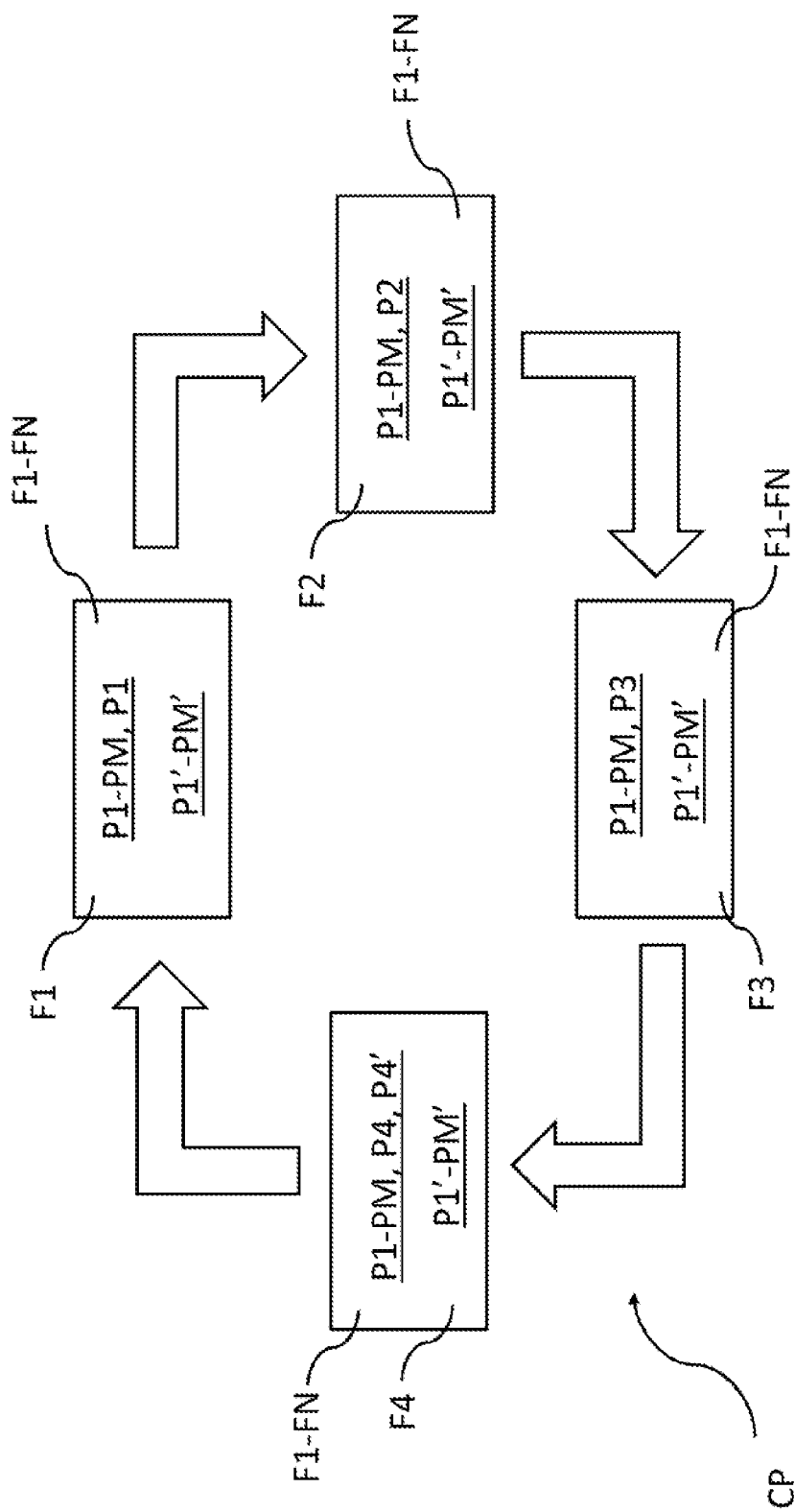
FIG. 4 diagrammatically shows a workout progression cycle which may be implemented in the system in FIG. 1.

It is worth noting that the control occurs according to a cycle CP of workout progression steps, diagrammatically shown in FIG. 4.

The cycle CP of workout progression steps comprises a plurality of workout progression steps F1-FN in a set order, stored in the memory module 301 of the remote electronic calculator 300.

Each workout progression step F1-FN comprises at least one respective workout parameter P1-PM of a user on the exercise machine 100.

In an embodiment, in combination with the preceding one, each workout progression step F1-FN comprises a plurality of workout parameters P1-PM of a user on the exercise machine 100.

Such workout parameters P1-PM of a user on an exercise machine 100 comprise:
- a number of repetitions within a series to be performed by the user;
- an execution rate of the recommended exercise; for the purposes of the present description, "execution rate" means the execution speed recommended for each exercise that can be performed by the user on the exercise machine 100 for strength workout;
- a recovery time between one series and a successive series;
- a number of series to be performed;
- an exercise load of the exercise machine 100 (and that is, the resistive load applied by the at least one motor 2 of the exercise machine 100); and
- test parameters representative of tests suggested to the user, including for example the so-called 1RM test, i.e., the test for checking the maximum load movable by the user in an individual repetition (1-Repetition Maximum, 1RM).

In an embodiment, the plurality of workout progression steps F1-FN, in the set order, comprises a first workout progression step F1 associated with at least one first workout parameter P1.

In an embodiment, in combination with the preceding one, the plurality of workout progression steps F1-FN, in the set order, further comprises a second workout progression step F2 associated with at least one second workout parameter P2.

In an embodiment, in combination with any of those defined above or alternatively to that comprising the second workout progression step F2, the plurality of workout progression steps F1-FN, in the set order, comprises a third workout progression step F3 associated with at least one third workout parameter P3.

In an embodiment, in combination with any of those defined above or alternatively to any of the preceding ones in which the second workout progression step F2 and the third workout progression step F3 are defined, the plurality of workout progression steps F1-FN further comprises a fourth workout progression step F4 associated with at least one fourth workout parameter P4.

Returning again to FIG. 1, the remote electronic calculator 300 is further configured to send, to the data processing unit 3 of the exercise machine 100, such workout parameters P1-PM of a user on the exercise machine 100, as described later.

Again, with reference to FIG. 1, the data processing module 301 of the remote electronic calculator 300 is configured to receive, from the data processing unit 3 of the exercise machine 100, at the end of each exercise performed by the user on the exercise machine 100, the first time data D1 of an exercise performed by the user and the second data D2 representative of a strength workout status achieved by the user with the exercise performed.

The data processing module 301 is configured to store, in the memory module 302, the first time data D1 of an exercise performed by the user and the second data D2 representative of a strength workout status achieved by the user with the exercise performed.

Moreover, the data processing module 301 is configured to store, in the memory module 302, on the basis of the first time data D1 of an exercise performed by the user and of the second data D2 representative of a strength workout status achieved by the user with the exercise performed, received each time at the end of each exercise performed by the user on the exercise machine, first pieces of time information I1 of strength workout previously performed by the user and second pieces of information I2 representative of strength workout statuses previously achieved by the user.

Such first pieces of time information I1 and second pieces of information I2 are described below.

Again, it is worth noting that the memory module 302 of the remote electronic calculator 300 is configured to store the plurality of workout progression steps F1-FN, each with the respective workout parameters P1-PM, in a set order, according to the respective cycle CP of workout progression steps.

According to an embodiment, in combination with any of those described above, the data processing module 301 of the remote electronic calculator 300 is configured checking that a trigger condition CS of a cycle CP of workout progression steps F1-FN is met by comparing the first pieces of time information I1 of strength workout previously performed by the user with respective reference values VRP and/or the second pieces of information I2 representative of strength workout statuses previously achieved by the user with respective reference values VRP'.

Such reference values VRP, VRP', which are described in greater detail below, are associated with a trigger condition CS, it also described in greater detail below, of a cycle CP of workout progression steps.

If the trigger condition CS of a cycle CP of workout progression steps is met, the data processing module 301 of the remote electronic calculator 300 is configured to acquire, from the memory module 302 of the remote electronic calculator 300, a last workout progression step F1-FN of the cycle CP of workout progression steps F1-FN performed by the user prior to the authentication on the exercise machine 100.

In this embodiment, the data processing module 301 of the remote electronic calculator 300 is configured to identify, as workout progression step F1-FN to be performed, a successive workout progression step F1-FN, in the set order provided by the cycle CP of workout progression steps F1-FN, with respect to the last workout progression step F1-FN of the cycle CP of workout progression steps F1-FN performed by the user prior to the authentication on the exercise machine 100 and stored in the memory module 302 of the remote electronic calculator 300.

With reference to the example in FIG. 4, the plurality of workout progression steps F1-FN comprises four steps, i.e., in the set order, a first workout progression step F1, a second workout progression step F2, a third workout progression step F3 and a fourth workout progression step F4.

Therefore, in this example, at the occurrence of a trigger condition CS, if the last workout progression step F1-FN of the cycle CP of workout progression steps F1-FN performed by the user prior to the authentication on the exercise machine 100 is the fourth workout progression step F4, the data processing module 301 of the remote electronic calculator 300 is configured to identify the first workout progression step F1 as workout progression step F1-FN to be performed.

Moreover, in an embodiment, the data processing module 301 of the remote electronic calculator 300 is configured to set the workout parameters P1-PM associated with the workout progression step F1-FN to be performed.

The workout progression step F1-FN to be performed is associated with a venation of at least one workout parameter P1-PM of the user on the exercise machine 100 for updating a previously set value of said at least one workout parameter P1-PM of the user on the exercise machine 100.

The data processing module 301 is configured to update the previously set value P1'-PM' of said at least one workout parameter P1-PM of the user on the exercise machine 100 according to the variation of said at least one workout parameter P1-PM of the user on the exercise machine 100 provided by the workout progression step F1-FN to be performed.

In an embodiment, if such a workout parameter P1-PM is the number of repetitions to be performed by the user within a series, the variation of said at least one workout parameter P1-PM of the user on the exercise machine 100 provided by the workout progression step F1-FN to be performed may be a set number of units (for example, +1, +2, and so on).

Therefore, in this embodiment, the updated value P1'-PM' corresponds to the previously set value increased by a set number of units.

In an embodiment, if such a workout parameter P1-PM is the execution rate of the exercise to be performed by the user, the variation of said at least one workout parameter P1-PM of the user on the exercise machine 100 provided by the workout progression step F1-FN to be performed may be a variation of a set percentage (for example, +5%, −5%, and so on) of the previously set value.

Therefore, in this embodiment, the updated value P1'-PM' corresponds to the previously set value varied by a set percentage of the previously set value.

In an embodiment, if such a workout parameter P1-PM is the recovery time between one series and a successive series provided by the exercise, the variation of said at least one workout parameter P1-PM of the user on the exercise machine 100 provided by the workout progression step F1-FN to be performed may be a decrease by a set number of seconds (for example, −20).

Therefore, in this embodiment, the updated value P1'-PM' corresponds to the previously set value decreased by a set number of seconds.

In an embodiment, if such a workout parameter is the maximum load movable by the user in an individual repetition (1-RM), the variation of said at least one workout parameter P1-PM of the user on the exercise machine 100 provided by the workout progression step F1-FN to be performed may be a variation of a set percentage (for example, +5%) of the previously set value.

Therefore, in this embodiment, the updated value P1'-PM' corresponds to the previously set value varied by a set percentage of the previously set value.

In an embodiment, alternative to the preceding one, if such a workout parameter is the maximum load movable by the user in an individual repetition (1-RM), the updated value of said at least one workout parameter P1-PM of the user on the exercise machine 100 provided by the workout progression step F1-FN to be performed is determined by performing the so-called 1-RM test.

Returning in general to the system 200 in FIG. 1, the data processing unit 301 is configured to send, to the data processing module 3 of the exercise machine 100, the workout parameters P1-PM of the user on the exercise machine 100, comprising the updated value P1'-PM' of the at least one workout parameter P1-PM of the user on the exercise machine 100.

The data processing module 301 is further configured to send, to the data processing unit 3 of the exercise machine 100, setting parameters of the exercise machine 100 which are required to perform an exercise.

With reference again to the exercise machine 100, the data processing unit 3 of the exercise machine 100 is configured to set the workout parameters P1-PM of the user on the exercise machine 100, received from the data processing module 301 of the remote electronic calculator 300, including the updated value P1'-PM' of the at least one workout parameter P1-P4 of the user on the exercise machine 100.

Moreover, the data processing unit 3 of the exercise machine 100 is configured to set, on the exercise machine 100, the setting parameters of the exercise machine 100 which are required to perform an exercise.

Moreover, it is worth noting that the data processing module 301 of the remote electronic calculator 300 is configured to receive a set workout goal provided by the user (for example, selected at the authentication moment on the exercise machine 100).

The data processing module 301 of the remote electronic calculator 300 is configured to select the variation of said at least one workout parameter P1-PM of the user on the exercise machine 100 provided by the workout progression step F1-FN to be performed, for updating a previously set value of said at least one workout parameter P1-PM of the user on the exercise machine 100, according to the set workout goal selected by the user.

Examples of workout goals may be increasing strength, losing weight, starting the movement, maintaining a youthful appearance, toning.

By way of example, if the workout goal is losing weight:

if the workout parameter P1-PM of the user on the exercise machine 100 is the number of repetitions to be performed by the user within a series, the variation of said at least one workout parameter P1-PM of the user on the exercise machine 100 provided by the workout progression step F1-FN to be performed may be +2. Therefore, the updated value P1'-PM' of number of repetitions to be performed by the user is the previously set value increased by two units;

if the workout parameter P1-P4 of the user on the exercise machine 100 is the recovery time between one series and a successive series, the variation of said at least one workout parameter P1-PM of the user on the exercise machine 100 provided by the workout progression step F1-FN to be performed may be −20 seconds. Therefore, the updated value P1'-PM' of recovery time is the previously set value decreased by 20 seconds.

Figure 5:
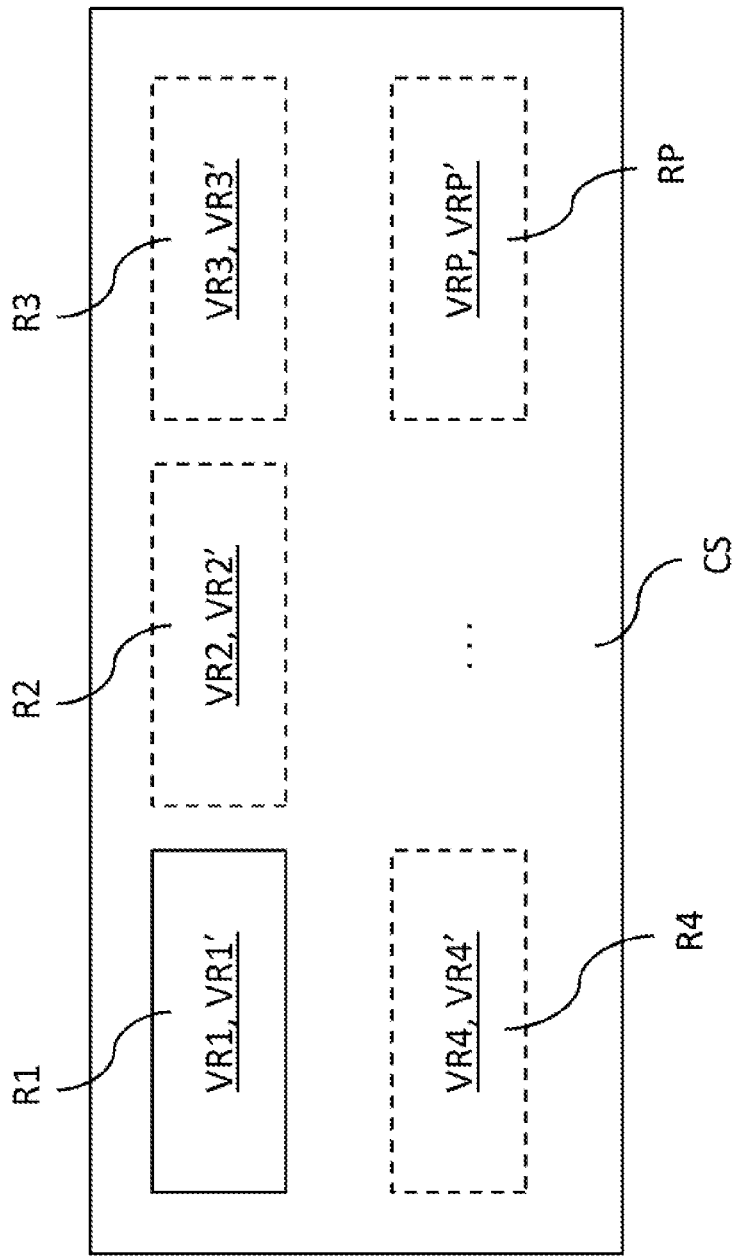
FIG. 5 diagrammatically shows a trigger condition of a workout progression step of the workout progression cycle in FIG. 4, and FIG. 6 diagrammatically shows, by means of a block diagram, a method for controlling at least one variation of workout parameters of a user on an exercise machine for strength workout, according to the present invention.

Referring now also to FIG. 5, in an embodiment, the trigger condition CS of a cycle CP of workout progression steps F1-FN, later also only trigger condition CS, comprises at least one first trigger rule R1.

In this embodiment, in order to check that the trigger condition CS of a cycle CP of workout progression steps F1-FN is met, the data processing module 301 of the remote electronic calculator 300 is configured to check the at least one first trigger rule R1 by comparing a first piece of time information of said first pieces of time information I1 of strength workout previously performed by the user with a respective first reference value VR1 and/or a first piece of information of said second pieces of information I2 representative of strength workout statuses previously achieved by the user with a respective second reference value VR1'.

The first reference value VR1 and the second reference value VR1' are associated with the at least one first trigger rule R1.

The at least one first trigger rule R1 is met if a condition is met between the first piece of time information of said first pieces of time information I1 of strength workout previously performed by the user and the respective first reference value VR1 and/or a condition between the first piece of information of said second pieces of information I2 representative of strength workout statuses previously achieved by the user and the respective second reference value VR1'.

The condition between the first piece of time information of said first pieces of time information I1 of strength workout previously performed by the user and the respective first reference value VR1 may be I1>VR1 or I1<VR1.

The condition between the first piece of information of said second pieces of information I2 representative of strength workout statuses previously achieved by the user and the respective second reference value VR1' may be I2>VR1' or I2<VR1'.

In an embodiment, in combination with the preceding one and shown in dashed lines in FIG. 5, the trigger condition CS comprises at least one second trigger rule R2.

In this embodiment, in order to check the trigger condition CS, the data processing module 301 of the remote electronic calculator 300 is configured to check the at least one second trigger rule R2 by comparing a second piece of time information of said first pieces of time information I1 of strength workout previously performed by the user with a respective first reference value VR2 and/or a second piece of information of said second pieces of information I2 representative of strength workout statuses previously achieved by the user with a respective second reference value VR2'.

The first reference value VR2 and the second reference value VR2' are associated with the at least one second trigger rule R2.

The at least one second trigger rule R2 is met if a condition is met between the second piece of time information of said first pieces of time information I1 of strength workout previously performed by the user and the respective first reference value VR2 and/or a condition between the second piece of information of said second pieces of information I2 representative of strength workout statuses previously achieved by the user and the respective second reference value VR2'.

The condition between the second piece of time information of said first pieces of time information I1 of strength workout previously performed by the user and the respective first reference value VR2 may be I1>VR2 or I1<VR2.

The condition between the second piece of information of said second pieces of information I2 representative of strength workout statuses previously achieved by the user and the respective second reference value VR2' may be I2>VR2' or I2<VR2'.

In this embodiment, the trigger condition CS is met if the at least one of the at least one first trigger rule R1 and the at least one second trigger rule R2 is met.

According to an embodiment, in combination with any of the preceding ones and shown in dashed lines in FIG. 5, the trigger condition comprises a plurality of trigger rules R1-RP.

In this embodiment, in order to check that the trigger condition CS is met, the data processing module 301 of the remote electronic calculator 300 is configured to check each trigger rule R1-RP of the plurality of trigger rules R1-RP by comparing, for each trigger rule R1-RP, a respective piece of time information of said first pieces of time information I1 of strength workout previously performed by the user with a respective first reference value VRP and/or a respective piece of time information of said second pieces of information I2 representative of strength workout statuses previously achieved by the user with a respective second reference value VRP'.

A trigger rule R1-RP is met if a condition is met between the respective piece of time information of said first pieces of time information I1 of strength workout previously performed by the user and the respective first reference value VRP and/or a condition between the respective piece of information of said second pieces of information I2 representative of strength workout statuses previously achieved by the user and the respective second reference value VRP'.

The condition between the respective piece of time information of said first pieces of time information I1 of strength workout previously performed by the user and the respective first reference value VRP may be I1>VRP or I1<VRP.

The condition between the second piece of information of said second pieces of information I2 representative of strength workout statuses previously achieved by the user and the respective second reference value VRP' may be I2>VRP' or I2<VRP'.

In this embodiment, the trigger condition CS is met if the at least one trigger rule R1-RP of said plurality of trigger rules R1-RP is met.

According to various embodiments, in combination with any of those described above, said first pieces of time information I1 of strength workout previously performed by the user comprise at least one among:

a time instant in which the user started a workout program;

a time instant in which the passage occurred from one workout progression step F1-FN to a successive workout progression step, in the set order, within a cycle CP of workout progression steps F1-FN; and a time instant in which the user performed a workout progression step F1-FN of the cycle CP of workout progression steps, of which the check that the trigger condition CS was met, was performed.

According to various embodiments, in combination with any of those described above, said second pieces of information I2 representative of strength workout statuses previously achieved by the user comprise at least one among:

a performance level achieved for a set number of workout sessions; and a number of workout sessions completed by the user.

If the trigger condition CS comprises the at least one first trigger rule R1, in an embodiment, the at least one first trigger rule R1 provides checking if the time instant in which the user started a workout program and/or the time instant in which the passage occurred from one workout progression step F1-FN to a successive workout progression step, in the set order, within a cycle CP of workout progression steps F1-FN, is greater than or equal to a respective first reference value VR1.

For example, the respective first reference value VR1 may be equal to a set number of days, for example seven.

In this embodiment, the at least one first trigger rule R1 further provides checking if the performance level achieved for a set number of workout sessions is greater than or equal to the respective second reference value VR1'.

For example, the second reference value VR1' may be 95%.

According to this embodiment, the at least one first trigger rule R1 is met if seven or more days have passed from the start time instant of the workout program or from the time instant in which the passage occurred from one workout progression step F1-FN to a successive workout progression step, in the set order, within a cycle CP of workout progression steps F1-FN and/or if the performance level achieved in the last two workout sessions was equal to 95% with respect to the expected performance.

According to an embodiment, in combination with the preceding one, in which the trigger condition also comprises the at least one second trigger rule R2, the at least one second trigger rule R2 further provides checking if the time instant in which the user performed a workout progression step F1-FN of the cycle CP of workout progression steps of which it was checked if the trigger condition CS was met, is greater than or equal to a respective first reference value VR2.

For example, the respective first reference value VR2 may be equal to a set number of days, for example thirty.

In this embodiment, the at least one second trigger rule R2 further provides checking if the number of workout sessions completed by the user is greater than or equal to a respective second reference value VR2'.

For example, the respective second reference value VR2' may be equal to a set number, for example eight.

According to this embodiment, the at least one second trigger rule R2 is met if thirty days have passed from the time instant in which the user performed a workout progression step F1-FN of the cycle CP of workout progression steps for which the check that the trigger condition CS and/or the number of workout sessions completed by the user is greater than or equal to eight, was met.

In embodiment, in combination with any of those described above, if the workout progression step F1-FN to be performed is the first workout progression step F1, the data processing module 301 of the remote electronic calculator 300 is configured to update the first previously set workout parameter P1-PM to the updated value P1'-PM'.

Thereby, following a new authentication of the user on the exercise machine 100, when the trigger condition CS is met and the workout progression step F1-FN to be performed, following the set order, is the first workout progression step F1, the at least one first workout parameter P1-PM is updated starting from the last updated value P1'-PM' of such at least one first workout parameter P1-PM.

Therefore, the workout progression allows increasing, for example, the number of repetitions that the user must perform in each series.

In a further embodiment, in combination with the preceding one, if the workout progression step F1-FN to be performed is the first workout progression step F1, the data processing module 301 of the remote electronic calculator 301 is configured to update the at least one second workout parameter P2 of the second workout progression step F2 and the at least one third workout parameter P3 of the third workout progression step F3 to a respective initial value.

Therefore, at each start of the cycle CP of workout progression steps, the execution rate of the workout by the user (third parameter P3) will always start from a respective initial value, for example equal to a repetition every 3 seconds, and the recovery time between one series and a successive series (fourth workout parameter P4) will always start from a respective initial value, for example equal to 60 seconds.

According to an embodiment, if the workout progression step F1-FN to be performed is the fourth workout progression step F4, the data processing unit 3 of the exercise machine 100 is configured to determine a current value P4' of said fourth workout parameter P4 representative of a maximum load movable by the user in an individual repetition.

In other words, when the fourth workout progression step F4 is set, the data processing unit 3 of the exercise machine 100 is configured to perform a test checking the so-called 1-RM of the user.

In this embodiment, the data processing unit 3 of the exercise machine 100 is configured to compare the determined current value P4' of the fourth workout parameter P4 with a value of said previously set fourth workout parameter P4.

If the determined current value P4' is greater than the previously set value of said fourth workout parameter P4, the data processing unit 3 of the exercise machine 100 is configured to set the determined current value P4' as value of said at least one fourth workout parameter representative of a maximum load movable by the user in an individual repetition.

If instead the determined current value is lower than the previously set value of said fourth workout parameter P4, the data processing unit 3 of the exercise machine 100 is configured to keep the previously set value as value of said at least one fourth workout parameter representative of a maximum load movable by the user in an individual repetition.

In an embodiment, alternative to the preceding one, if the workout progression step to be performed is the fourth workout progression step F4, the data processing module 301 of the remote electronic calculator 300 is configured to increase the previously set value of said fourth workout parameter P4 by a set percentage (for example, +5%) of the previously set value.

In this embodiment, the data processing module 301 of the remote electronic calculator 300 is configured to set the increased value as value of said at least one fourth workout parameter representative of a maximum load movable by the user in an individual repetition.

In an embodiment, in combination with that described above, in which a test is performed checking the so-called 1-RM of the user, the data processing unit 3 of the exercise machine 100 is configured to communicate the set value of said fourth workout parameter P4 to the data processing module 301 of the remote electronic calculator 300.

In an embodiment, according to any of those described above, the data processing module 301 of the remote electronic calculator 300 is configured to store, in the memory module 302 of the remote electronic calculator 300, the identified workout progression step F1-FN to be performed as last workout progression step F1-FN performed prior to a new authentication of the user on the exercise machine 100.

Thereby, upon the new authentication of the user on the exercise machine 100 and if the trigger condition CS is met, the cycle CP of workout progression steps F1-FN will resume from the workout progression step F1-FN following the last workout progression step stored in the memory module 302 of the remote electronic calculator 300, therefore following the last one to have been performed by the user on the exercise machine 100.

According to an embodiment, in combination with any other one of those described above, the data processing unit 3 of the exercise machine 100 is configured to display, on a respective display module 7 of the exercise machine 100, the updated value P1'-PM' of said at least one workout parameter P1-PM of the user on the exercise machine 100 during the execution of the set workout progression step.

Figure 6:
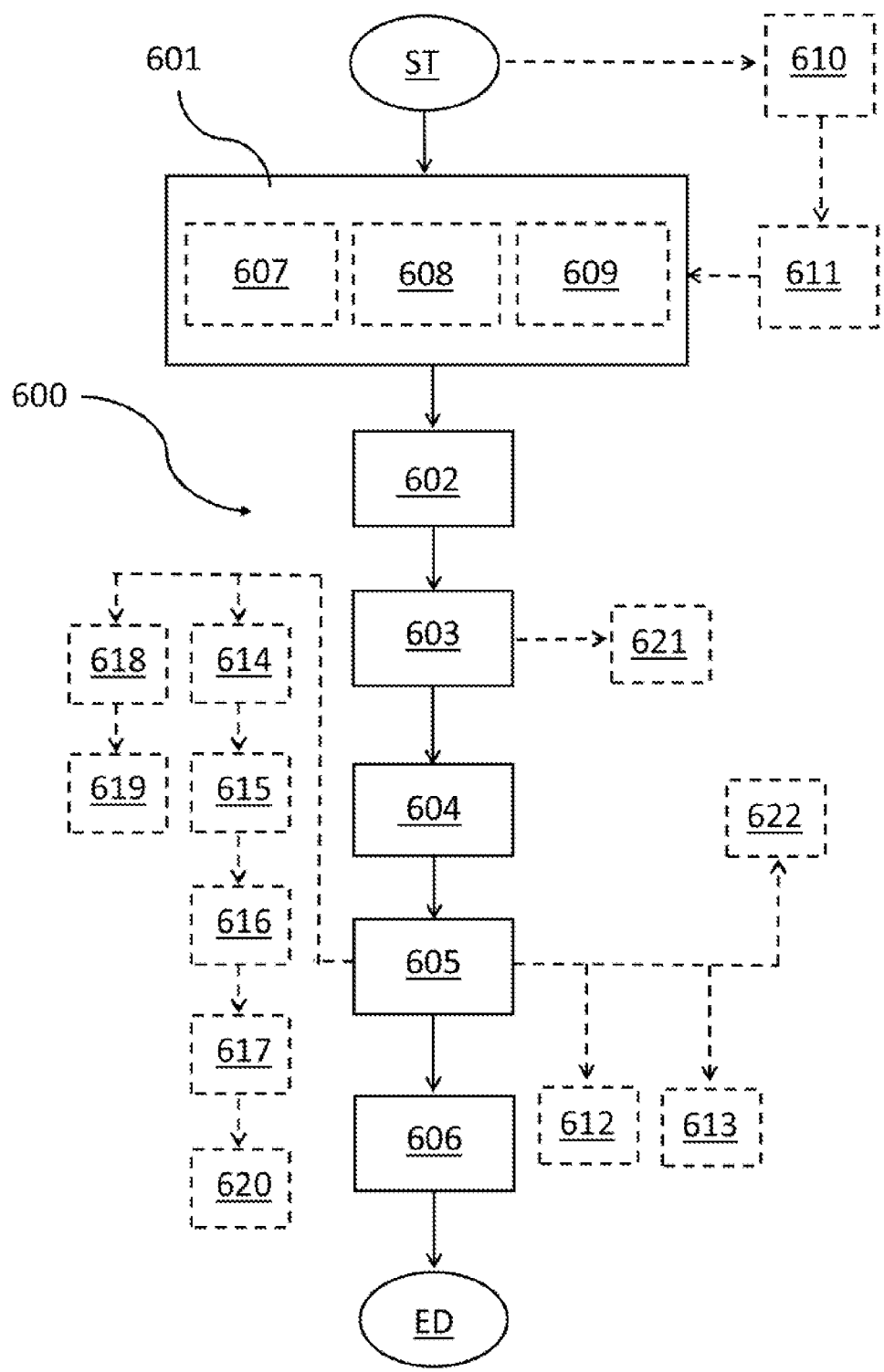

With reference now also to FIG. 6, a method 600 for controlling at least one venation of workout parameters P1-PM of a user on an exercise machine 100 for strength workout, later also control method 600 or simply method 600, according to the present invention, is described.

The method 600 is performed in a cycle CP of workout progression steps comprising a plurality of workout progression steps F1-FN in a set order, already described above.

Each workout progression step F1-FN comprises at least one respective workout parameter P1-PM of a user on the exercise machine 100.

The workout parameters P1-PM were already described above.

The method 600 comprises an operating symbolic step of starting ST.

The method 600 comprises an operating step of s1) checking 601, by a data processing module 301 of a remote electronic calculator 300 operatively connected to the exercise machine 100, following the authentication of the user on the exercise machine 100, that a trigger condition CS of a cycle CP of workout progression steps F1-FN is met by comparing first pieces of time information I1 of strength workout previously performed by the user with respective reference values VRP and/or second pieces of information I2 representative of strength workout statuses previously achieved by the user with respective reference values VRP'.

The reference values VRP, VRP' are associated with a trigger condition CS of a cycle CP of workout progression steps.

If the trigger condition CS of a cycle CP of workout progression steps is met, the method 600 comprises an operating step of s2) acquiring 602, by the data processing module 301 of the remote electronic calculator 300, from a memory module 302 of the remote electronic calculator 300, a last workout progression step F1-FN of the cycle CP of workout progression steps performed by the user prior to the authentication on the exercise machine 100.

The method 600 comprises an operating step of s3) identifying 603, by the data processing module 301 of the remote electronic calculator 300, as workout progression step F1-FN to be performed, a successive workout progression step F1-FN, in the set order provided by the cycle CP of workout progression steps F1-FN, with respect to the last workout progression step F1-FN of the cycle CP of workout progression steps F1-FN performed by the user prior to the authentication on the exercise machine 100 and stored in the memory module 302 of the remote electronic calculator 300.

The method 600 comprises an operating step of s4) setting 604, by the data processing module 301 of the remote electronic calculator 300, the workout parameters P1-PM associated with the workout progression step F1-FN to be performed.

The workout progression step F1-FN to be performed is associated with a venation of at least one workout parameter P1-PM of the user on the exercise machine 100 for updating a previously set value of said at least one workout parameter P1-PM of the user on the exercise machine 100.

The method 600 comprises an operating step of s5) updating 605, by the data processing module 301 of the remote electronic calculator 300, the previously set value P1'-PM' of said at least one workout parameter P1-PM of the user on the exercise machine 100 according to the variation of said at least one workout parameter P1-PM of the user on the exercise machine 100 provided by the workout progression step F1-FN to be performed.

The method 600 further comprises an operating step of s6) sending 606, to a data processing unit 3 of the exercise machine 100, by the data processing module 301 of the remote electronic calculator 300, the workout parameters P1-PM of the user on the exercise machine 100, comprising the updated value P1'-PM' of the at least one workout parameter P1-PM of the user on the exercise machine 100.

According to an embodiment, in combination with the preceding one, the trigger condition CS comprises at least one first trigger rule R1.

In this embodiment, shown in dashed lines in FIG. 6, the operating step of s1) checking 601 comprises an operating step of s7) checking 607, by the data processing module 301 of the remote electronic calculator 300, the at least one first trigger rule R1 by comparing a first piece of time information of said first pieces of time information I1 of strength workout previously performed by the user with a respective first reference value VR1 and/or a first piece of information of said second pieces of information I2 representative of strength workout statuses previously achieved by the user with a respective second reference value VR1'.

The first reference value VR1 and the second reference value VR1' are associated with the at least one first trigger rule R1.

The at least one first trigger rule R1 is met if a condition is met between the first piece of time information of said first pieces of time information I1 of strength workout previously performed by the user and the respective first reference value VR1 and/or a condition between the first piece of information of said second pieces of information I2 representative of strength workout statuses previously achieved by the user and the respective second reference value VR1'.

In an embodiment, in combination with the preceding one and shown in dashed lines in FIG. 5, the trigger condition CS comprises at least one second trigger rule R2.

In this embodiment, in combination with the preceding one and shown in dashed lines in FIG. 6, the operating step of s1) checking 601 comprises an operating step of s8) checking 608, by the data processing module 301 of the remote electronic calculator 300, the at least one second trigger rule R2 by comparing a second piece of time information of said first pieces of time information I1 of strength workout previously performed by the user with a respective first reference value VR2 and/or a second piece of information of said second pieces of information I2 representative of strength workout statuses previously achieved by the user with a respective second reference value VR2'.

The first reference value VR2 and the second reference value VR2' are associated with the at least one second trigger rule R2.

The at least one second trigger rule R2 is met if a condition is met between the second piece of time information of said first pieces of time information I1 of strength workout previously performed by the user and the respective first reference value VR2 and/or a condition between the second piece of information of said second pieces of information I2 representative of strength workout statuses previously achieved by the user and the respective second reference value VR2'.

In this embodiment, the trigger condition CS is met if the at least one of the at least one first trigger rule R1 and the at least one second trigger rule R2 is met.

According to an embodiment, in combination with any of the preceding ones and shown in dashed lines in FIG. 5, the trigger condition CS comprises a plurality of trigger rules R1-RP.

In this embodiment, shown in dashed lines in FIG. 6, the operating step of s1) checking 601 comprises an operating step of s9) checking 609, by the data processing module 301 of the remote electronic calculator 300, each trigger rule R1-RP of the plurality of trigger rules R1-RP by comparing, for each trigger rule R1-RP, a respective piece of time information of said first pieces of time information I1 of strength workout previously performed by the user with a respective first reference value VRP and/or a respective piece of information of said second pieces of information I2 representative of strength workout statuses previously achieved by the user with a respective second reference value VRP'.

A trigger rule R1-RP is met if a condition is met between the respective piece of time information of said first pieces of time information I1 of strength workout previously performed by the user and the respective first reference value VRP and/or a condition between the respective piece of information of said second pieces of information I2 representative of strength workout statuses previously achieved by the user and the respective second reference value VRP'.

In this embodiment, the trigger condition CS is met if the at least one trigger rule R1-RP of said plurality of trigger rules R1-RP is met.

According to various embodiments, in combination with any of those described above, said first pieces of time information I1 of strength workout previously performed by the user comprise at least one among:
- a time instant in which the user started a workout program;
- a time instant in which the passage occurred from one workout progression step F1-FN to a successive workout progression step, in the set order, within a cycle CP of workout progression steps F1-FN; and
- a time instant in which the user performed a workout progression step F1-FN of the cycle CP of workout progression steps, of which the check that the trigger condition CS was met, was performed.

According to various embodiments, in combination with any of those described above, said second pieces of information I2 representative of strength workout statuses previously achieved by the user comprise at least one among:
- a performance level achieved for a set number of workout sessions; and
- a number of workout sessions completed by the user.

According to an embodiment, if the trigger condition CS comprises the at least one first trigger rule R1, the at least one first bigger rule R1 provides checking if the time instant in which the user started a workout program and/or the time instant in which the passage occurred from one workout progression step F1-FN to a successive workout progression step, in the set order, within a cycle CP of workout progression steps F1-FN, is greater than or equal to a respective first reference value VR1.

For example, the respective first reference value VR1 may be equal to a set number of days, for example seven.

In this embodiment, the at least one first trigger rule R1 further provides checking if the performance level achieved for a set number of workout sessions has always been greater than or equal to the respective second reference value VR1'.

For example, the second reference value VR1' may be the total of the exercise load lifted for a given session (for example, 1000 kg).

According to this embodiment, the at least one first trigger rule R1 is met if seven or more days have passed from the start time instant of the workout program or from the time instant in which the passage occurred from one workout progression step F1-FN to a successive workout progression step, in the set order, within a cycle CP of workout progression steps F1-FN and/or if the performance level achieved in the last two workout sessions was equal to the lifting of 1000 kg within each session.

According to an embodiment, in combination with the preceding one, in which when the trigger condition CS also comprises the at least one second trigger rule R2, the at least one second trigger rule R2 provides checking if the time instant in which the user performed a workout progression step F1-FN of the cycle CP of workout progression steps of which it was checked if the trigger condition CS was met, is greater than or equal to a respective first reference value VR2.

For example, the respective first reference value VR2 may be equal to a set number of days, for example thirty.

In this embodiment, the at least one second trigger rule R2 further provides checking if the number of workout sessions completed by the user is greater than or equal to a respective second reference value VR2'.

For example, the respective second reference value VR2' may be equal to a set number, for example eight.

According to this embodiment, the at least one second trigger rule R2 is met if thirty days have passed from the time instant in which the user performed a workout progression step F1-FN of the cycle CP of workout progression steps for which the check that the trigger condition CS and/or the number of workout sessions completed by the user is greater than or equal to eight, was met.

According to an embodiment, according to any of those described above and shown in dashed lines in FIG. 6, the method 600 comprises an operating step of s10) receiving 610, by the data processing module 301 of the remote electronic calculator 300, a set workout goal provided by the user (for example, selected at the time of authentication on the exercise machine 100).

In this embodiment, the method 600 comprises an operating step of s11) selecting 611, by the data processing module 301 of the remote electronic calculator 300, the variation of said at least one workout parameter P1-PM of the user on the exercise machine 100 provided by the workout progression step F1-FN to be performed, for updating a previously set value of said at least one workout parameter P1-PM of the user on the exercise machine 100, according to the set workout goal selected by the user.

Examples of workout goals were provided above.

In an embodiment, according to any of those described above, the plurality of workout progression steps F1-FN, in the set order, comprises a first workout progression step F1 associated with at least one first workout parameter P1.

The at least one first workout parameter P1 is a number of repetitions within a series to be performed by the user.

In an embodiment, in combination with the preceding one, the plurality of workout progression steps F1-FN, in the set order, further comprises a second workout progression step F2 associated with at least one second workout parameter P2.

The at least one second workout parameter P2 is a recommended execution rate of an exercise.

In an embodiment, in combination with any of those defined above or alternatively to that comprising the second workout progression step F2, the plurality of workout progression steps F1-FN, in the set order, comprises a third workout progression step F3 associated with at least one third workout parameter P3.

The at least one third workout parameter P3 is a recovery time between one series and a successive series.

In an embodiment, in combination with any of those defined above or alternatively to any of the preceding ones in which the second workout progression step F2 and the third workout progression step F3 are defined, the plurality of workout progression steps F1-FN further comprises a fourth workout progression step F4 associated with at least one fourth workout parameter P4.

The at least one fourth workout parameter P4 is a test parameter, representative of a maximum load movable by the user in an individual repetition (1-RM).

According to an embodiment, according to any of those described above in which the workout progression steps F1-FN are defined and shown in dashed lines in FIG. 6, the method 600 comprises, if the workout progression step F1-FN to be performed is the first workout progression step F1, an operating step of s12) updating 612, by the data processing module 301 of the remote electronic calculator 300, the first previously set workout parameter P1-PM to the updated value P1'-PM'.

According to an embodiment, according to any of those described above in which the workout progression steps F1-FN are defined and shown in dashed lines in FIG. 6, the method 600 comprises, if the workout progression step F1-FN to be performed is the first workout progression step F1, an operating step of s13) updating 613, by the data processing module 301 of the remote electronic calculator 300, the at least one second workout parameter P2 of the second workout progression step F2 and the at least one third workout parameter P3 of the third workout progression step F3, to a respective initial value.

According to an embodiment, according to any of those described above in which the workout progression steps F1-FN are defined, if the workout progression step F1-FN to be performed is the fourth workout progression step F4, the method 600 further comprises operating steps of:

s14) determining 614, by the data processing unit 3 of the exercise machine 100, a current value P4' of said at least one fourth workout parameter P4 representative of a maximum load movable by the user in an individual repetition; and s15) comparing 615, by the data processing unit 3 of the exercise machine 100, the determined current value P4' with a previously set value of said at least one fourth workout parameter P4.

If the determined current value P4' is greater than the previously set value of said at least one fourth workout parameter P4, the method 600 comprises an operating step of s16) setting 616, by the data processing unit 3 of the exercise machine 100, the determined current value P4' as value of said at least one fourth workout parameter representative of a maximum load movable by the user in an individual repetition.

If instead the determined current value is lower than the previously set value of said at least one fourth workout parameter P4, the method 600 comprises an operating step of s17) keeping 617, by the data processing unit 3 of the exercise machine 100, the previously set value as value of said at least one fourth workout parameter representative of a maximum load movable by the user in an individual repetition.

According to an embodiment, alternative to the preceding one and shown in dashed lines in FIG. 6, the method 600 comprises, if the workout progression step to be performed is the fourth workout progression step F4, operating steps of:

s18) increasing 618, by the data processing module 301 of the remote electronic calculator 300, the previously set value of said at least one fourth workout parameter P4 by a set percentage (for example, +5%) of the previously set value; and s19) setting 619, by the data processing module 301 of the remote electronic calculator 300, the increased value as value of said at least fourth workout parameter representative of a maximum load movable by the user in an individual repetition.

In an embodiment, in combination with the preceding one in which a test is performed checking the so-called 1-RM of the user and shown in dashed lines in FIG. 6, the method 600 comprises an operating step of s20) communicating 620, by the data processing unit 3 of the exercise machine 100, the set value of said at least one fourth workout parameter P4 to the data processing module 301 of the remote electronic calculator 300.

In an embodiment, according to any of those described above and shown in dashed lines in FIG. 6, the method 600 further comprises an operating step of s21) storing 621, by the data processing module 301 of the remote electronic calculator 300, in the memory module 302 of the remote electronic calculator 300, the identified workout progression step F1-FN to be performed as last workout progression step F1-FN performed prior to a new authentication of the user on the exercise machine 100.

Thereby, upon the new authentication of the user on the exercise machine 100 and if the trigger condition CS is met, the cycle CP of workout progression steps F1-FN will resume from the workout progression step F1-FN following the last workout progression step stored in the memory module 302 of the remote electronic calculator 300, therefore following the last one to have been performed by the user on the exercise machine 100.

According to an embodiment, in combination with any of those described above and shown in dashed lines in FIG. 6, the method 600 further comprises an operating step of s22)

displaying 622, by the data processing unit 3 of the exercise machine 100, on a respective display module 7 of the exercise machine 100, the updated value P1'-PM' of said at least one workout parameter P1-PM of the user on the exercise machine 100 during the execution of the set workout progression step.

The method 600 comprises an operating symbolic step of ending ED.

With reference to FIGS. 1, 4 and 5, an example of implementing the method for controlling at least one variation of workout parameters of a user on an exercise machine for strength workout, according to the present invention, is described.

A user is authenticated on an exercise machine 100 for strength workout and selects a set workout goal.

A data processing module 301 of a remote electronic calculator 300 operatively connected to the exercise machine 100 checks that a trigger condition CS of a cycle CP of workout progression steps F1-FN is met by comparing first pieces of time information I1 of strength workout previously performed by the user with respective reference values VRP and/or second pieces of information I2 representative of strength workout statuses previously achieved by the user with respective reference values VRP'.

The reference values VRP, VRP' are associated with a trigger condition CS of a cycle CP of workout progression steps.

In particular, the data processing module 301 of the remote electronic calculator 300 checks if the at least one first trigger rule R1 is met by comparing a first piece of time information of said first pieces of time information I1 of strength workout previously performed by the user with a respective first reference value VR1 and/or a first piece of information of said second pieces of information I2 representative of strength workout statuses previously achieved by the user with a respective second reference value VR1'.

The first reference value VR1 and the second reference value VR1' are associated with the at least one first trigger rule R1.

The data processing module 301 of electronic calculator 300 checks if a condition between the first piece of time information of said first pieces of time information I1 of strength workout previously performed by the user and the respective first reference value VR1, is met.

Therefore, the at least one first trigger rule R1, therefore the trigger condition CS, is met.

The data processing module 301 of the remote electronic calculator 300:

acquires, from a memory module 302 of the remote electronic calculator 300, a last workout progression step F1-FN of the cycle CP of workout progression steps performed by the user prior to the authentication on the exercise machine 100;

identifies, as workout progression step F1-FN to be performed, a successive workout progression step F1-FN, in the set order provided by the cycle CP of workout progression steps F1-FN, with respect to the last workout progression step F1-FN of the cycle CP of workout progression steps F1-FN performed by the user prior to the authentication on the exercise machine 100 and stored in the memory module 302 of the remote electronic calculator 300;

sets the workout parameters P1-PM associated with the workout progression step F1-FN to be performed;

updates the previously set value P1'-PM' of said at least one workout parameter P1-PM of the user on the exercise machine 100 according to the variation of said at least one workout parameter P1-PM of the user on the exercise machine 100 provided by the workout progression step F1-FN to be performed; and sends, to a data processing unit 3 of the exercise machine 100, the workout parameters P1-PM of the user on the exercise machine 100, comprising the updated value P1'-PM' of the at least one workout parameter P1-PM of the user on the exercise machine 100.

The data processing module 301 of the remote electronic calculator 300 stores, in the respective memory module 302, the identified workout progression step F1-FN to be performed as last workout progression step performed by the user.

The data processing unit 3 of the exercise machine 100 sets, on the exercise machine 100, the workout parameters P1-P4 and further setting parameters received from the data processing module 301 of the remote electronic calculator 300.

The user performs the exercise on the exercise machine 100 while displaying, on a respective display module 7 of the exercise machine 100, the updated value P1'-PM' of the at least one workout parameter P1-PM of the user on the exercise machine 100.

At the end of the exercise, the data processing unit 3 automatically sends, to the remote electronic calculator 300, first time data D1 of the exercise performed by the user on the exercise machine 100 and second data D2 representative of a strength workout status achieved by the user with the exercise performed, on the basis of which the data processing module 301 of the remote electronic calculator 300 updates and stores, in the respective memory module 302, the first pieces of time information I1 of strength workout previously performed by the user and the second pieces of information I2 representative of strength workout statuses previously achieved by the user which will be used again for checking the presence or absence of a trigger condition CS at a new authentication of the user on an exercise machine 100.

It is worth noting that the scope of the invention is fully achieved.

Indeed, the method and related system according to the present invention allow obtaining an improvement at the performance level because the exercise machine provided allows performing exercises for controlled strength workout, thus ensuring the most performing and reliable execution by the user with respect to a principle of workout progressivity which, inter alia, also takes into consideration the workout goals for which the workout is performed.

Those skilled in the art may make changes and adaptations to the embodiments of the method and system described above or can replace elements with others which are functionally equivalent in order to meet contingent needs without departing from the scope of the following claims. Each of the features described as belonging to a possible embodiment can be achieved irrespective of the other embodiments described.

What is claimed is:

1. A method for controlling at least one variation of workout parameters of a user on an exercise machine for strength workout, in a cycle of workout progression steps comprising a plurality of workout progression steps in a set order, each workout progression step comprising a respective workout parameter, the method comprising operating steps of:

s1) checking, by a data processing module of a remote electronic calculator operatively connected to the exercise machine, following authentication of the user on the exercise machine, that a trigger condition of the cycle of workout progression steps is met by comparing first pieces of time information of strength workout previously performed by the user with respective reference values and/or second pieces of information representative of strength workout statuses previously achieved by the user with respective reference values, said reference values being associated with the trigger condition of a cycle of workout progression steps;

if the trigger condition of a cycle of workout progression steps is met, s2) acquiring, by the data processing module of the remote electronic calculator, from a memory module of the remote electronic calculator, a last workout progression step of the cycle of workout progression steps performed by the user prior to authentication on the exercise machine;

s3) identifying, by the data processing module of the remote electronic calculator, as workout progression step to be performed, a successive workout progression step, in the set order provided by the cycle of workout progression steps, with respect to the last workout progression step of the cycle of workout progression steps performed by the user prior to authentication on the exercise machine and stored in the memory module of the remote electronic calculator;

s4) setting, by the data processing module of the remote electronic calculator, the workout parameters associated with the workout progression step to be performed, the workout progression step to be performed having associated a variation of at least one workout parameter of the user on the exercise machine for updating a previously set value of said at least one workout parameter of the user on the exercise machine;

s5) updating, by the data processing module of the remote electronic calculator, the previously set value of said at least one workout parameter of the user on the exercise machine according to the variation of said at least one workout parameter of the user on the exercise machine provided by the workout progression step to be performed; and s6) sending, to a data processing unit of the exercise machine, by the data processing module of the remote electronic calculator, the workout parameters of the user on the exercise machine, comprising the updated value of the at least one workout parameter of the user on the exercise machine.

2. The method of claim 1, wherein the trigger condition comprises at least one first trigger rule, the operating step s1) of checking comprising an operating step of:

s7) checking, by the data processing module of the remote electronic calculator, the at least one first trigger rule by comparing a first piece of time information of said first pieces of time information of strength workout previously performed by the user with a respective first reference value and/or a first piece of information of said second pieces of information representative of strength workout statuses previously achieved by the user with a respective second reference value, the first reference value and the second reference value being associated with the at least one first trigger rule, the at least one first trigger rule being met if a condition is met between the first piece of time information of said first pieces of time information of strength workout previously performed by the user and the respective first reference value and/or a condition is met between the first piece of information of said second pieces of information representative of strength workout statuses previously achieved by the user and the respective second reference value.

3. The method of claim 2, wherein the trigger condition comprises at least one second trigger rule, the operating step s1) of checking comprising an operating step of:

s8) checking, by the data processing module of the remote electronic calculator, the at least one second trigger rule by comparing a second piece of time information of said first pieces of time information of strength workout previously performed by the user with a respective first reference value and/or a second piece of information of said second pieces of information representative of strength workout statuses previously achieved by the user with a respective second reference value, the first reference value and the second reference value being associated with the at least one second trigger rule, the at least one second trigger rule being met if a condition is met between the second piece of time information of said first pieces of time information of strength workout previously performed by the user and the respective first reference value and/or a condition is met between the second piece of information of said second pieces of information representative of strength workout statuses previously achieved by the user and the respective second reference value, the trigger condition being met if at least one between the at least one first trigger rule and the at least one second trigger rule is met.

4. The method of claim 1, wherein the trigger condition comprises a plurality of trigger rules, the operating step s1) of checking comprising an operating step of s9) checking, by the data processing module of the remote electronic calculator, each trigger rule of the plurality of trigger rules by comparing, for each trigger rule, a respective piece of time information of said first pieces of time information of strength workout previously performed by the user with a respective first reference value and/or a respective piece of information of said second pieces of information representative of strength workout statuses previously achieved by the user with a respective second reference value, a trigger rule being met if a condition is met between the respective piece of time information of said first pieces of time information of strength workout previously performed by the user and the respective first reference value and/or a condition is met between the respective piece of information of said second pieces of information representative of strength workout statuses previously achieved by the user and the respective second reference value, the trigger condition being met if at least one trigger rule of said plurality of trigger rules is met.

5. The method of claim 2, wherein said first pieces of time information of strength workout previously performed by the user comprise at least one among:

a time instant in which the user started a workout program;

a time instant in which a passage occurred from one workout progression step to a successive workout progression step, in the set order, within a cycle of workout progression steps; and a time instant in which the user performed a workout progression step of the cycle of workout progression steps, of which checking that the trigger condition was met, was performed.

6. The method of claim 1, wherein said second pieces of information representative of strength workout statuses previously achieved by the user comprise at least one between:

a performance level achieved for a set number of workout sessions; and a number of workout sessions completed by the user.

7. The method of claim 5, wherein if the trigger condition comprises the at least one first trigger rule, the at least one first trigger rule provides checking if the time instant in which the user started a workout program and/or the time instant in which a passage occurred from one workout progression step to a successive workout progression step, in the set order, within a cycle of workout progression steps, is greater than or equal to the respective first reference value, the at least one first trigger rule further providing checking if the performance level achieved for a set number of workout sessions is greater than or equal to the respective second reference value.

8. The method of claim 5, wherein when the trigger condition also comprises the at least one second trigger rule, the at least one second trigger rule provides checking if the time instant in which the user performed a workout progression step of the cycle of workout progression steps of which checking if the trigger condition was met, is greater than or equal to the respective first reference value, the at least one second trigger rule further providing checking if the number of workout sessions completed by the user is greater than or equal to the respective second reference value.

9. The method of claim 1, comprising operating steps of:
s10) receiving, by the data processing module of the remote electronic calculator, a set workout goal selected by the user; and
s11) selecting, by the data processing module of the remote electronic calculator, the variation of said at least one workout parameter of the user on the exercise machine provided by the workout progression step to be performed, for updating the previously set value of said at least one workout parameter of the user on the exercise machine, according to the set workout goal selected by the user.

10. The method of claim 1, wherein the plurality of workout progression steps, in the set order, comprises a first workout progression step associated with at least one first workout parameter, the at least one first workout parameter being a number of repetitions within a series to be performed by the user.

11. The method of claim 10, wherein the plurality of workout progression steps, in the set order, further comprises a second workout progression step associated with at least one second workout parameter, the at least one second workout parameter being a recommended execution rate of an exercise.

12. The method of claim 10, wherein the plurality of workout progression steps, in the set order, comprises a third workout progression step associated with at least one third workout parameter, the at least one third workout parameter being a recovery time between one series and a successive series.

13. The method of claim 10, wherein the plurality of workout progression steps further comprises a fourth workout progression step associated with at least one fourth workout parameter, the at least one fourth workout parameter being a test parameter, representative of a maximum load movable by the user in an individual repetition.

14. The method of claim 10, comprising, in the event the workout progression step to be performed is the first workout progression step, an operating step of:
s12) updating, by the data processing module of the remote electronic calculator, the at least one first workout parameter previously set to the updated value.

15. The method of claim 10, comprising, in the event the workout progression step to be performed is the first workout progression step, an operating step of:
s13) updating, by the data processing module of the remote electronic calculator, the at least one second workout parameter of the second workout progression step and the at least one third workout parameter of the third workout progression step to a respective initial value.

16. The method of claim 10, comprising, in the event the workout progression step to be performed is the fourth workout progression step, operating steps of:
s14) determining, by the data processing unit of the exercise machine, a current value of said at least one fourth workout parameter representative of a maximum load movable by the user in an individual repetition;
s15) comparing, by the data processing unit of the exercise machine, the current value determined with a previously set value of said at least one fourth workout parameter,
in the event the current determined value is greater than the previously set value of said at least one fourth workout parameter, the method comprising an operating step of:
s16) setting, by the data processing unit of the exercise machine, the determined current value as value of said at least one fourth workout parameter representative of a maximum load movable by the user in an individual repetition; or
in the event the current determined value is lower than the previously set value of said at least one fourth workout parameter,
s17) keeping, by the data processing unit of the exercise machine, the previously set value as value of said at least one fourth workout parameter representative of a maximum load movable by the user in an individual repetition.

17. The method of claim 10, comprising, in the event the workout progression step to be performed is the fourth workout progression step, operating steps of:
s18) increasing, by the data processing module of the remote electronic calculator, the previously set value of said at least one fourth workout parameter by a set percentage of the previously set value; and
s19) setting, by the data processing module of the remote electronic calculator, the increased value as value of said at least one fourth workout parameter representative of a maximum load movable by the user in an individual repetition.

18. The method of claim 16, comprising an operating step of:
s20) communicating, by the data processing unit of the exercise machine, the set value of said at least one fourth workout parameter to the data processing module of the remote electronic calculator.

19. The method of claim 1, further comprising an operating step of:
s21) storing, by the data processing module of the remote electronic calculator, in the memory module of the remote electronic calculator, the identified workout progression step) to be performed as last workout progression step performed prior to a new authentication of the user on the exercise machine.

20. The method of claim 1, further comprising an operating step of:
s22) displaying, by the data processing unit of the exercise machine, on a respective display module of the exercise machine, the updated value of said at least one workout parameter of the user on the exercise machine during execution of the set step of workout progression.

21. A system for controlling at least one variation of workout parameters of a user on an exercise machine for strength workout, in a cycle of workout progression steps comprising a plurality of workout progression steps in a set order, each workout progression step comprising a respective workout parameter, the system comprising:
- at least one exercise machine for strength workout, comprising:
  - at least one movable element operable by the user to execute a strength exercise by handling a respective exercise load;
  - at least one electric motor operatively connected to said at least one movable element, the at least one electric motor being configured to exert, on the at least one movable element, a resistive force representative of an exercise load which the user may handle during execution of the exercise by actuating the at least one movable element; and
  - a data processing unit operatively connected to said at least one electric motor; and
- a remote electronic calculator operatively connected to the at least one exercise machine for strength workout, the remote electronic calculator comprising a data processing module,
- the data processing module of the remote electronic calculator being configured to:
  - check, following authentication of the user on the exercise machine, that a trigger condition of a cycle of workout progression steps is met by comparing first pieces of time information of strength workout previously performed by the user with respective reference values and/or second pieces of information representative of strength workout statuses previously achieved by the user with respective reference values, said reference values being associated with the trigger condition of a cycle of workout progression steps;
  - if the trigger condition of a cycle of workout progression steps is met, acquire, a last workout progression step of the cycle of workout progression steps performed by the user prior to authentication on the exercise machine;
  - identify, as workout progression step to be performed, a successive workout progression step, in the set order provided by the cycle of workout progression steps, with respect to the last workout progression step of the cycle of workout progression steps performed by the user prior to authentication on the exercise machine and stored in the memory module of the remote electronic calculator;
  - set the workout parameters associated with the workout progression step to be performed, the workout progression step to be performed having associated a variation of at least one workout parameter of the user on the exercise machine for updating a previously set value of said at least one workout parameter of the user on the at least one exercise machine;
  - update the previously set value of said at least one workout parameter of the user on the exercise machine according to the variation of said at least one workout parameter of the user on the at least one exercise machine provided by the workout progression step to be performed; and
  - send, to a data processing unit of the exercise machine, the workout parameters of the user on the at least one exercise machine, comprising the updated value of the at least one workout parameter of the user on the at least one exercise machine.

* * * * *